US00PP14392P29

(12) United States Plant Patent
Repp

(10) Patent No.: US PP14,392 P2
(45) Date of Patent: Dec. 23, 2003

(54) COLEUS PLANT NAMED 'TOUCH OF CLASS'

(50) Latin Name: *Coleus×hybrida*
Varietal Denomination: Touch of Class

(76) Inventor: Ralph Repp, 423 Country Rd., Waynesville, NC (US) 28785

( * ) Notice: Subject to any disclaimer, the term of this patent is extended or adjusted under 35 U.S.C. 154(b) by 0 days.

(21) Appl. No.: 10/291,102

(22) Filed: Nov. 8, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—A Para
(74) *Attorney, Agent, or Firm*—C. A. Whealy

(57) ABSTRACT

A new and distinct cultivar of Coleus plant named 'Touch of Class', characterized by its upright, mounded and compact plant habit; and pale yellow and green bi-colored leaves with red-purple colored venation and petioles.

1 Drawing Sheet

Botanical classification/cultivar designation: Coleus×hybrida cultivar Touch of Class.

BACKGROUND OF THE INVENTION

The present Invention relates to a new and distinct cultivar of Coleus plant, botanically known as *Solenostemon scutellarioides*, and hereinafter referred to by the cultivar name Touch of Class.

The new cultivar was discovered by the Inventor in a controlled environment in Waynesville, N.C. as a seedling from a cross-pollination of two unidentified selections of *Solenostemon scutellarioides*, not patented. The new Coleus was observed within the seedling progeny from the stated cross-pollination. This seedling was selected on the basis of its unique leaf coloration.

Asexual reproduction of the new cultivar by terminal cuttings taken in Waynesville, N.C., has shown that the unique features of this new Coleus are stable and reproduced true to type in successive generations.

SUMMARY OF THE INVENTION

Plants of the cultivar Touch of Class have not been observed under all possible environmental conditions. The phenotype may vary somewhat with variations in environment such as temperature and light intensity without, however, any variance in genotype.

The following traits have been repeatedly observed and are determined to be the unique characteristics of 'Touch of Class'. These characteristics in combination distinguish 'Touch of Class' as a new and distinct cultivar:

1. Upright and mounded plant habit.
2. Pale yellow and green bi-colored leaves with red purple-colored venation and petioles.

Plants of the new Coleus are most similar to plants of the parent selections. Plants of the new Coleus differ from plants of the parent selections in foliage color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Coleus.

The photograph at the top of the sheet comprises a side perspective view of typical plant of 'Touch of Class' grown in a container.

The photograph at the bottom of the sheet comprises a closeup view of typical leaves of 'Touch of Class'.

DETAILED BOTANICAL DESCRIPTION

The cultivar Touch of Class has not been observed under all possible environmental conditions. The phenotype may vary somewhat with variations in environment such as temperature and light intensity without, however, any variance in genotype.

The aforementioned photographs, following observations and measurements describe plants grown during the winter and spring in Encinitas, Calif., in an outdoor nursery and under conditions which approximate commercial production cultural and environmental conditions. Plants were about 14 weeks from rooted cuttings and were grown in one-gallon containers. During the production of the plants, day temperatures averaged 24° C. and night temperatures averaged 19° C.

In the following description, color references are made to The Royal Horticultural Society Colour Chart, 1995 Edition, except where general terms of ordinary dictionary significance are used.

Botanical classification: *Solenostemon scutellarioides* cultivar Touch of Class.

Parentage: Seedling from a cross-pollination of two unidentified selections of *Solenostemon scutellarioides*, not patented.

Propagation:

*Type cutting.*—Terminal cuttings.

*Time to initiate roots.*—Summer: About 4 days at 21° C. Winter: About 5 to 6 days at 21° C.

*Time to develop roots.*—Summer: About 14 days at 20° C. Winter: About 14 to 17 days at 20° C.

*Root description.*—Fine, fibrous, white in color.

*Rooting habit.*—Freely branching.

Plant description:

*Form.*—Annual flowering plant; upright and mounded. Rapid growth rate.

*Plant height.*—About 54 cm.

*Plant diameter.*—About 64 cm.

*Branching habit.*—Freely branching with potentially two lateral branches forming at every node.

*Lateral branches.*—Length: About 50 cm. Diameter: About 1.3 cm. Internode length: About 6 cm. Shape, in cross-section: Squarish. Texture: Glabrous. Color: 187A.

*Foliage description: Arrangement: Opposite; simple. Length: About* 9.5 cm. Width: About 6.7 cm. Shape: Elliptic. Apex: Acute. Base: Attenuate to truncate. Margin: Crenate, scalloped; ruffled. Texture, upper and lower surfaces: Glabrous. Venation pattern: Pinnate. Color: Young foliage, upper surface: Center, 151B; towards margins, 144A to 144B. Young foliage, lower surface: 144A to 144B. Fully expanded foliage, upper surface: Center, 10D; towards margins, 144A to 144B; at margin, 59A. Fully expanded foliage, lower surface: Center, 10D; towards margins, 144B; towards base, blushed with 61B. Venation, upper surface: 59B. Venation, lower surface: 59B to 59C. Petiole length: About 4 mm. Petiole diameter: About 3 mm. Petiole color: 59B.

Flower description: Flower development has not been observed.

Disease/pest resistance: Plants of the new Coleus have not been noted to be resistant to pathogens or pests common to Coleus.

Temperature tolerance: Plants of the new Coleus have been observed to tolerate temperatures from 2 to 35° C.

It is claimed:

1. A new and distinct cultivar of Coleus plant named 'Touch of Class', as illustrated and described.

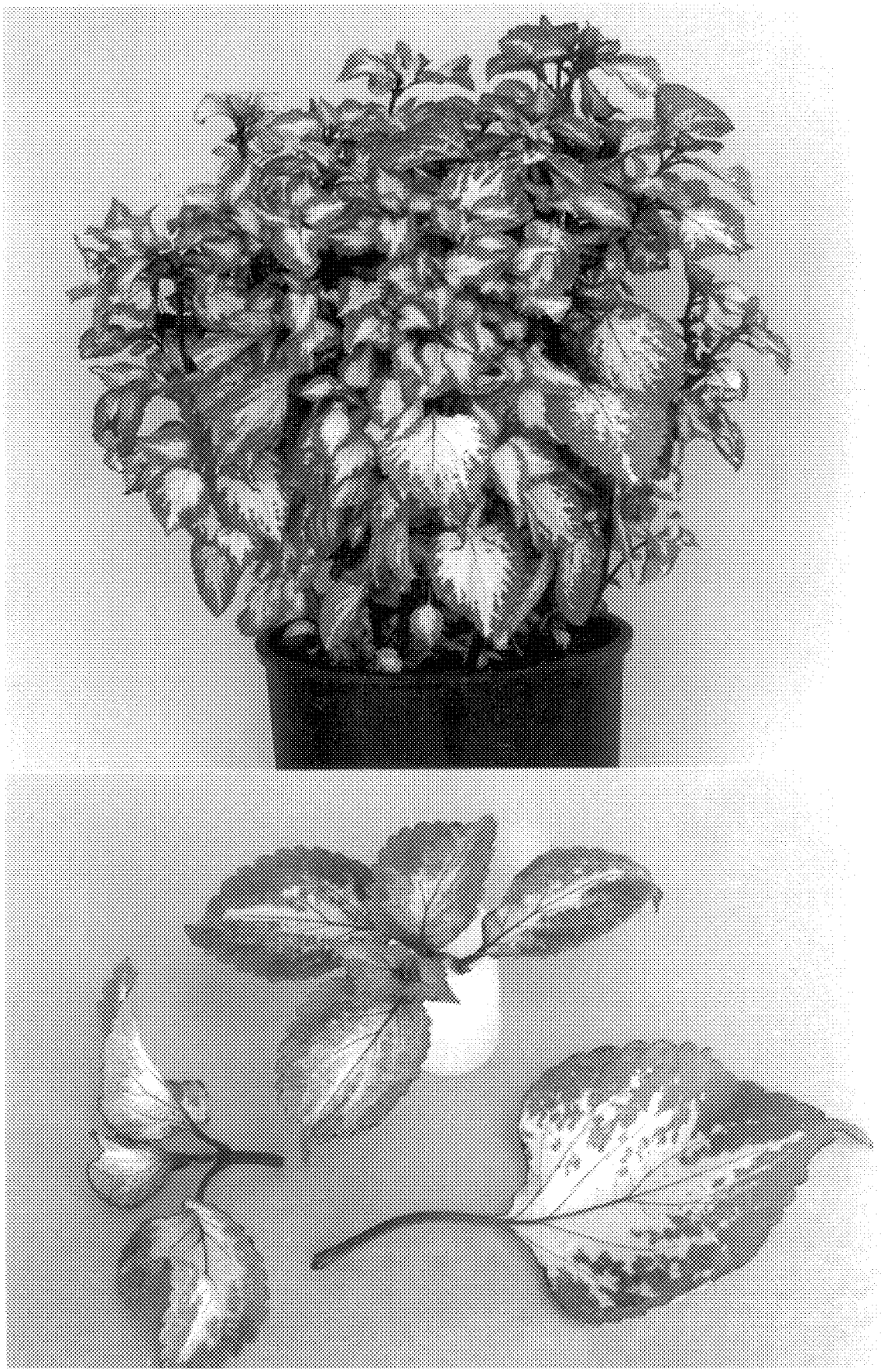

* * * * *